United States Patent [19]

Shephard et al.

[11] 4,113,465
[45] Sep. 12, 1978

[54] HERBICIDAL FORMULATIONS

[75] Inventors: Margaret Claire Shephard, Maidenhead; Balsubramanyan Sugavanam, Wokingham; Paul Anthony Worthington, Maidenhead; David John Collins, Crowthorne; David Griffin, Maidenhead, all of England

[73] Assignee: Imperial Chemical Industries Limited, London, England

[21] Appl. No.: 750,017

[22] Filed: Dec. 13, 1976

[30] Foreign Application Priority Data

Dec. 16, 1975 [GB] United Kingdom ............... 51458/75

[51] Int. Cl.² ...................... A01N 9/22; C07D 249/08
[52] U.S. Cl. ............................................. 71/92; 71/76; 260/308 R; 424/269; 424/273 R; 548/341
[58] Field of Search ................ 71/92, 88, 76, 123, 71/107; 424/269; 260/308 R

[56] References Cited

U.S. PATENT DOCUMENTS

| | | | |
|---|---|---|---|
| 2,855,439 | 10/1958 | Kundiger et al. | 71/123 |
| 3,013,079 | 12/1961 | Pearson et al. | 71/123 |
| 3,205,058 | 9/1965 | Leasure | 71/123 |
| 3,598,564 | 8/1971 | Jacobi et al. | 71/107 |
| 3,754,001 | 8/1973 | Timmler et al. | 260/308 R |
| 3,967,949 | 7/1976 | Benefiel et al. | 71/88 |
| 4,007,278 | 2/1977 | Hubele | 71/92 |

OTHER PUBLICATIONS

Hancock et al., "The Behavior of Phlorizin, etc.;" (1961) CA 56, pp. 15862–15863 (1962).
Wiley et al., "Conjugate Add'n, Reactions, etc.," (1955), JACS 77, pp. 2572–2573 (1955).

*Primary Examiner*—Glennon H. Hollrah
*Attorney, Agent, or Firm*—Cushman, Darby & Cushman

[57] ABSTRACT

Herbicidal and fungicidal compounds of the formula:

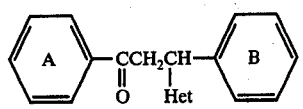

wherein rings A and B are unsubstituted or carry one or more substituents which may be lower alkyl, halogen, lower alkoxy, cyano, nitro, lower alkylcarbonyloxy, methylene dioxy, amino, or mono- or dialkyl amino, and Het is a 1,2,4-triazolyl or imidazolyl group.

8 Claims, No Drawings

HERBICIDAL FORMULATIONS

This invention relates to novel imidazole and triazole derivatives which are useful as herbicides and fungicides, and to a process for preparing them. The invention also relates to herbicidal and fungicidal compositions containing these compounds, or containing 2-phenyl-2-(1,2,4-triazol-1-yl) propiophenone (a known compound) and to methods of combatting fungal infections of plants and of killing plants using said compounds.

According to the present invention, there are provided fungicidal and herbicidal compounds of the formula:

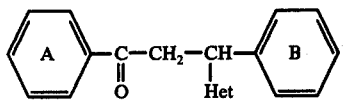

wherein rings A and B are unsubstituted, or carry one or more substituents, each substituent being a lower alkyl radical; a fluorine, chlorine, bromine, or iodine atom; a lower alkoxy radical; a cyano group; a nitro group; a lower alkylcarbonyloxy radical; a methylenedioxy radical; an amino group; or a mono- or di- lower alkyl-substituted amino group, at least one of the rings A and B being substituted; and salts of compounds of the foregoing formula. The substituents on rings A and B may be different.

By lower alkyl and lower alkoxy we mean groups containing from 1 to 6 carbon atoms, for example methyl, ethyl, propyl, butyl, methoxy, ethoxy, propoxy and butoxy groups.

The compounds of the invention include, for example, compounds wherein ring A is unsubstituted and ring B is substituted. Preferred compounds for fungicidal uses include compounds wherein ring A is unsubstituted and ring B bears a 2-halogeno substituted, for example a 2-fluoro or 2-chloro substitutent.

Examples of salts of compounds according to the invention include salts formed from alkali metals, alkaline earth metals, ammonia, or primary, secondary or tertiary amines in which the one, two, or three aliphatic radicals each contain from one to six carbon atoms.

Being carbonyl compounds, the novel compounds of the invention and the known compound referred to above form derivatives typical of that class of compound, for example oximes, hydrazones, semicarbazones, and thiosemicarbazones. Insofar as these derivatives possess biological activity similar to that of the parent carbonyl compounds, the derivatives, and their use in the processes of the invention form further features of the invention.

Particular examples of compounds according to the invention are listed in Table I, together with their melting points.

TABLE I

| Compound No. | Het | Ring A | Ring B | Melting Point °C |
|---|---|---|---|---|
| 1 | T | U | U | 78-79 |
| 2 | T | 3,4-Cl | U | 68-71 |
| 3 | I | U | U | 75-76 |
| 4 | T | U | 4-Cl | 114-115 |

TABLE I-continued

| Compound No. | Het | Ring A | Ring B | Melting Point °C |
|---|---|---|---|---|
| 5 | T | U | 2,4-Cl | 132-133 |
| 6 | T | U | 2-Cl | 86-88 |
| 7 | T | U | 3,4-Cl | 83-84 |
| 8 | T | U | 2,6-Cl | 117-118 |
| 9 | T | 4-Cl | U | 103-105 |
| 10 | T | 2,5-Cl | U | 102-105 |
| 11 | T | 2,4-Cl | U | 78-81 |
| 12 | T | 4-Cl | 2-Cl | 120-122 |
| 13 | T | 4-F | U | 55-57 |
| 14 | T | 4-Br | U | 130-132 |
| 15 | T | 4-F | 4-isoC$_3$H$_7$ | 108-110 |
| 16 | T | 2,4-CH$_3$ | 2-Cl | 94-96 |
| 17 | T | 4-CH$_3$ | 3,4-Cl | 117-119 |
| 18 | T | 4-OCH$_3$ | 3,4-Cl | 133-134 |
| 19 | T | 2,4-CH$_3$ | 2,6-Cl | Oil |
| 20 | T | 4-Cl | 3,4-Cl | 133-136 |
| 21 | T | 4-Cl | 3,4-OCH$_3$ | 134-136 |
| 22 | T | U | 4-OCH$_3$ | 103-105 |
| 23 | T | 4-OCH$_3$ | 2-Cl | 150-152 |
| 24 | T | 4-F | 4-CH$_3$ | 113-115 |
| 25 | T | 4-F | 4-N(CH$_3$)$_2$ | 95-97 |
| 26 | T | U | 3-CH$_3$ | 97-99 |
| 27 | T | U | 4-OCH$_3$ | 128-131 |
| 28 | T | 4-Cl | 4-isoC$_3$H$_7$ | 101-103 |
| 29 | T | 4-F | 2-Cl | 92-94 |
| 30 | T | 2,4-CH$_3$ | 3,4-Cl | 107-108 |
| 31 | T | U | 3-NO$_2$ | 132-134 |
| 32 | T | 4-OCH$_3$ | 3-NO$_2$ | 140-141 |
| 33 | T | 4-NHCOCH$_3$ | U | 173-174 |
| 34 | T | U | 3-CN | 125-126 |
| 35 | T | U | 2-OCH$_3$ | 109-110 |
| 36 | T | U | 2-F | 94-95 |
| 37 | T | U | 3,4-OCH$_2$O— | Decomposes |
| 38 | T | 4-Br | 2-Cl | 146-147 |
| 39 | T | 4-C$_2$H$_5$ | 2-Cl | 108-109 |
| 40 | T | U | 2-Br | 98-99 |
| 41 | T | U | 2-OC$_2$H$_5$ | 85-86 |
| 42 | T | U | 2-CH$_3$ | 86-87 |
| 43 | T | U | 2—OCCH$_3$ (=O) | 119-120 |
| 44 | T | 3,4-Cl | 2-OCH$_3$ | 124-126 |
| 45 | T | 4-F | 2-OCH$_3$ | 101-102 |
| 46 | T | U | 3-CF$_3$ | 93-94 |
| 47 | T | U | 3,4-OCH$_3$ | 105-107 |
| 48 | T | U | 4-Br | 122-124 |
| 49 | T | U | 3-Cl | 50-51 |
| 50 | T | U | 4-CH$_3$ | 138-139 |
| 51 | T | U | 3-F | Oil, $n_D^{20}$ = 1.585 |

U stands for unsubstituted.
T stands for triazole.
I stands for imidazole.

The compounds can be prepared by reacting imidazole or 1,2,4-triazole with the appropriate α,β-unsaturated ketone. The reaction may be performed by techniques known in the art. For example, 1,2,4-triazole can be reacted with a compound of general formula (II):

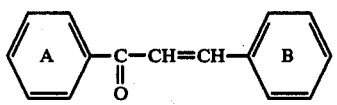

wherein rings A and B are as defined above, to give the triazole compounds of the invention. This process is preferably carried out by reacting, suitably under heating, the reactants together in the absence of a solvent or diluent or a base catalyst. The process may however be carried out in the presence of a base catalyst (e.g. pyridine or Triton B, i.e. trimethylbenzylammonium hydroxide). The product can be purified by recrystallisation from a solvent e.g. absolute ethanol or carbon disulphide.

The α,β-unsaturated ketone starting materials may be made by methods known in the art.

The above compounds and 2-phenyl-2-(1,2,4-triazol-1-yl) propiophenone and salts thereof are active fungicides particularly against the following diseases of plants:

*Piricularia oryzae* on rice

*Puccinia recondita, Puccinia striiformis* and other rusts on wheat, *Puccinia hordei, Puccinia striiformis* and other rusts on barley, and rusts on other hosts e.g. coffee, apples, vegetables and ornamental plants

*Plasmopara viticola* on vines

*Erysiphe graminis* (powdery mildew) on barley and wheat and other powdery mildews on various hosts such as *Sphaerotheca fuliginea* on cucurbits (e.g. cucumber), *Podosphaera leucotricha* on apples and *Uncinula necator* on vines

*Botrytis cinerea* (grey mould) on tomatoes, strawberries, vines and other hosts

*Phytophthora infestans* (blight) on tomatoes

Some of the compounds have also shown a broad range of activities against fungi in vitro. Further some of the compounds are active as seed dressings against: *Fusarium spp., Septoria spp., Tilletia spp., Ustilago spp.*, and *Pyrenophora spp.* on cereals.

The compounds also have certain plant growth regulating activities (particularly a stunting effect on the vegetative growth of mono- or di-cotyledonous plants), and antibacterial and anti-viral activities.

The compounds may be used as such for fungicidal purposes but are more conveniently formulated into compositions for such usage. The invention thus provides also a fungicidal composition comprising a compound of general formula (I) or a salt thereof and a carrier or diluent.

The invention also provides a method of combating fungal diseases in a plant, which method comprises applying to the plant, to seed of the plant or to the locus of the plant or seed a compound or salt or complex thereof as hereinbefore defined.

The compounds can be used to combat plant fungi and treat plants or seeds in a number of ways, for example they can be applied, formulated or unformulated, directly to the foliage of a plant which is infected or likely to become infected, or they can be applied also to bushes and trees, to seeds or to other medium in which plants, bushes or trees are growing or are to be planted, or they can be sprayed on, dusted on or applied as a cream or paste formulation. Application can be to any part of the plant, bush or tree, for example to the foliage, stems, branches or roots, or to soil surrounding the roots, or to the seed before it is planted.

The term "plant" as used herein includes seedlings, bushes and trees. Furthermore, the method of the invention includes preventative, protectant, prophylactic and eradicant treatment.

The compounds are preferably used for agricultural and horticultural purposes in the form of a composition. The type of composition used in any instance will depend upon the particular purpose envisaged.

The compositions may be in the form of dusting powders or granules comprising the active ingredient and a solid diluent or carrier, for example, kaolin, bentonite, kieselguhr, dolomite, calcium carbonate, talc, powdered magnesia, Fuller's earth, gypsum, Hewitt's earth, diatomaceous earth and China clay. Compositions for dressing seed, for example, may comprise an agent (for example a mineral oil) for assisting the adhesion of the composition to the seed.

The compositions may also be in the form of dispersible powders or grains comprising a wetting agent to facilitate the dispersion in liquids of the powder or grains which may contain also fillers and suspending agents.

The aqueous dispersions or emulsions may be prepared by dissolving the active ingredient(s) in an organic solvent optionally containing wetting, dispersing or emulsifying agent(s) and then adding the mixture to water which may also contain wetting, dispersing or emulsifying agent(s). Suitable organic solvents are ethylene dichloride, isopropyl alcohol, propylene glycol, diacetone alcohol, toluene, kerosene, methylnaphthalene, the xylenes and trichloroethylene.

The compositions to be used as sprays may also be in the form of aerosols wherein the formulation is held in a container under pressure in the presence of a propellant, e.g. fluorotrichloromethane or dichlorodifluoromethane.

By including suitable additives, for example additives for improving the distribution, adhesive power and resistance to rain on treated surfaces, the different compositions can be better adapted for various utilities.

The compounds can be used as mixtures with fertilisers (e.g. nitrogen - or phosphorus - containing fertilisers). Compositions comprising only granules of fertiliser incorporating, for example coated with, the compound, are preferred. The invention therefore also provides a fertiliser composition comprising the compound of general formula (I) or a salt thereof.

The compositions may also be in the form of liquid preparations for use as dips or sprays which are generally aqueous dispersions or emulsions containing the active ingredient in the presence of one or more wetting agent(s), dispersing agent(s), emulsifying agent(s) or suspending agent(s). These agents can be cationic, anionic or nonanionic agents. Suitable cationic agents are quaternary ammonium compounds, for example cetyltrimethylammonium bromide.

Suitable anionic agents are soaps, salts of aliphatic monoesters of sulphuric acid (for example sodium lauryl sulphate), and salts of sulphonated aromatic compounds (for example sodium dodecylbenzenesulphonate, sodium, calcium or ammonium lignosulphonate, butylnaphthalene sulphonate, and a mixture of sodium diisopropyl - and triisopropyl-naphthalene sulphonates).

Suitable non-ionic agents are the condensation products of ethylene oxide with fatty alcohols such as oleyl or cetyl alcohol, or with alkyl phenols such as octyl- or nonylphenol and octylcresol. Other non-ionic agents are the partial esters derived from long chain fatty acids and hexitol anhydrides, the condensation products of the said partial esters with ethylene oxide, and the lecithins. Suitable suspending agents are hydrophilic colloids (for example polyvinylpyrrolidone and sodium carboxymethylcellulose), and the vegetable gums (for example gum acacia and gum tragacanth).

The compositions for use as aqueous dispersions or emulsions are generally supplied in the form of a concentrate containing a high proportion of the active ingredient(s), the concentrate to be diluted with water before use. These concentrates often should be able to withstand storage for prolonged periods and after such storage be capable of dilution with water in order to form aqueous preparations which remain homogeneous for a sufficient time to enable them to be applied by conventional spray equipment. The concentrates may conveniently contain 10–85%, generally 25–60%, by weight of the active ingredient(s). When diluted to form aqueous preparations, such preparations may contain varying amounts of the active ingredient(s) depending upon the intended purpose, but an aqueous preparation containing 0.0005% or 0.01% to 10% by weight of active ingredient(s) may be used.

The compositions of this invention can comprise also other compound(s) having biological activity (e.g. growth stimulating substances such as the gibberellins and other compounds having complementary fungicidal or insecticidal activity), as well as stabilising agent(s), for example epoxides (e.g. epichlorhydrin).

The compounds are also active herbicides. The herbicidal activity is particularly noticed in the pre-emergent herbicide test.

In another aspect, therefore, the invention further provides a method of killing or severely damaging unwanted plants, which comprises applying to the plants, or to the locus of the plants, an effectively lethal or severely damaging amount of a compound of the formula:

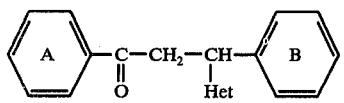

wherein rings A and B are unsubstituted, or carry one or more substituents, each substituent being a lower alkyl radical; a fluorine, chlorine, bromine, or iodine atom, a lower alkoxy radical; a cyano group; a nitro group; a lower alkylcarbonyloxy radical; a methylenedioxy radical; an amino group; or a mono- or di-alkyl substituted amino group; and wherein Het stands for 1,2,4-triazol-1-yl or imidazol-1-yl radical; or a salt of a compound of the last foregoing formula.

The compounds are relatively more phytotoxic towards species of grasses (Graminae) than towards broadleaved plants. They may therefore be used as selective herbicides for inhibiting the growth of weed grasses in broadleaved crops. The selective herbicidal activity is quite unusual, particularly post-emergence, it being more common to find that a herbicide can be used selectively to control broadleaved weeds occurring in graminaceous crops.

In a further aspect, therefore, the invention provides a method of selectively inhibiting the growth of grass weeds in broadleaved crops, which comprises applying to the crop, or to the locus thereof, a compound of the last foregoing formula, in an amount sufficient to inhibit the growth of grass weeds but insufficient substantially to damage the crop.

The rate at which the compounds are applied will depend upon a number of factors, for example, the identity of the particular compound selected for use, and the plant species to be killed or severely damaged. However, generally an amount of 0.25 to 10 kilograms per hectare is preferred. The skilled worker in the art will readily be able to ascertain suitable application rates by routine standardised procedures without undue experimentation.

The compounds are preferably applied in the form of a composition comprising the compound in admixture with a carrier comprising a solid diluent or a liquid diluent containing a surface-active agent.

The compositions can be both dilute compositions, which are ready for immediate use, and concentrated compositions, which require dilution before use, usually with water. Preferably the compositions contain 0.01% to 90% by weight of the active ingredient.

Dilute compositions ready for use preferably contain 0.01 to 2% by weight of active ingredient, while concentrated compounds may contain 20 to 90%, preferably 20 to 70%, by weight of active ingredient.

Solid compositions may be in the form of a powder containing a powdered solid diluent, for example, Fuller's earth, powdered kaolin, gypsum, chalk and kieselguhr. Such solid compositions may be applied as foliar dusts.

Liquid compositions may comprise a solution or dispersion of the active ingredient in water optionally containing a surface-active agent, or may comprise a solution or dispersion of an active ingredient in a water-immicible organic solvent which is dispersed as droplets in water.

The surface-active agent can be for example the products of condensation of ethylene oxide with alkyl-substituted phenols such as octyl- and nonyl-phenol; sorbitan monolaurate; oleyl alcohol; and propylene oxide polymer. A particular example of such a condensation products is Lissapol. Other examples are calcium dodecylbenzenesulphonate, and calcium, sodium, and ammonium lignosulphonates.

A preferred form of concentrated composition comprises the active ingredient finely divided and dispersed in water in the presence of a surface-active agent and a suspending agent. Preferred suspending agents are those which impart thixotropic properties to, and increase the viscosity of, the concentrate.

Examples are hydrated colloidal mineral silicates, such as montmorillonite, beidellite, nontronite, hectorite, saponite, and saucorite. Bentonite is especially preferred. Other suspending agents are cellulose derivatives and polyvinyl alcohol.

The known compound, 2-phenyl-2-(1,2,4-triazol-1-yl) propiophenone (Compound 1), and its preparation, is disclosed in Wiley, Smith, Johnson and Moffat (J.A.C.S. 1955, 77, 2572 – 73). It has a melting point of 78°–79° C.

The invention is illustrated by the following Examples:

EXAMPLE 1

This Example illustrates the preparation of compound No. 2 of Table I.

Benzal-3', 4'-dichloroacetophenone (13.8 g; 0.05 mol) and 1,2,4-triazole (3.4 g; 0.05 mol) were fused together at 120°–140° for 30 minutes. After cooling to room temperature, diethyl ether (10.0 ml) was added to precipitate the unreacted benzal 3',4'-dichloroacetophenone which was filtered off. The filtrate was concentrated to give a solid residue which, on crystallisation from carbon disulphide/absolute ethanol gave 2-phenyl-2-(1,2,4-triazol-1-yl)-3',4'-dichloropropiophenone (compound 2), m.p. 68°–71° C.

EXAMPLE 2

This Example illustrates the preparation of compound No. 3 of Table I.

Benzalacetophenone (4.2 g, 0.02 mol) and imidazole (1.34 g, 0.02 mol) were warmed over a flame for 30 minutes. After cooling to room temperature, the oil was treated with carbon disulphide to give, as colourless crystals, 2-phenyl2-(imidazol-1-yl) propiophenone (compound 3) m.p. 75°–76° C.

The compounds of Table I were prepared by this method or by the method of Example 1, using the appropriate starting materials.

EXAMPLE 3

An emulsifiable concentrate was made up by mixing together the ingredients set out below in the proportions stated and stirring the mixture until all the constituents were dissolved.

| | |
|---|---|
| Compound 1 | 10% |
| Ethylene Dichloride | 40% |
| Calcium dodecylbenzenesulphonate | 5% |
| "Lubrol" L | 10% |
| "Aromasol" H | 35% |

EXAMPLE 4

A composition in the form of grains readily dispersible in a liquid, e.g. water, was prepared by grinding together the first three of the ingredients listed below in the presence of added water and then mixing in the sodium acetate. The resultant mixture was dried and passed through a British Standard mesh sieve, size 44–100, to obtain the desired size of grains.

| | |
|---|---|
| Compound 2 | 50% |
| "Dispersol" T | 25% |
| "Lubrol" APN 5 | 1.5% |
| Sodium acetate | 23.5% |

EXAMPLE 5

The ingredients listed below were ground together in the proportions stated to produce a powder formulation readily dispersible in liquids.

| | |
|---|---|
| Compound 4 | 45% |
| "Dispersol" T | 5% |
| "Lissapol" NX | 0.5% |
| "Cellofas" B600 | 2% |
| Sodium acetate | 47.5% |

EXAMPLE 6

The active ingredient was dissolved in acetone and the resultant liquid was sprayed on to granules of China clay. The solvent was then allowed to evaporate to produce a granular composition.

| | |
|---|---|
| Compound 6 | 5% |
| China clay granules | 95% |

EXAMPLE 7

A composition suitable for use as a seed dressing was prepared by mixing the substances set out below in the proportions stated.

| | |
|---|---|
| Compound 7 | 50% |
| Mineral oil | 2% |
| China clay | 48% |

EXAMPLE 8

A dusting powder was prepared by mixing, in the proportions stated, the active ingredient with talc.

| | |
|---|---|
| Compound 1 | 5% |
| Talc | 95% |

EXAMPLE 9

A flowable paste was prepared by ball-milling the constituents set out below and then forming an aqueous suspension of the ground mixture with water.

| | |
|---|---|
| Compound 2 | 40% |
| "Dispersol" | 10% |
| "Lubrol" | 1% |
| Water | |

EXAMPLE 11

A dispersible powder formulation was made by mixing together the ingredients set out below and then grinding the mixture until all the constituents were thoroughly mixed.

| | |
|---|---|
| Compound 10 | 25% |
| "Aerosol" OT/B | 2% |
| "Dispersol" A.C. | 5% |
| China clay | 28% |
| Silicca | 40% |

EXAMPLE 12

This Example illustrates the preparation of a dispersible powder formulation. The ingredients were mixed in the proportions stated and the mixture then ground in a comminution mill.

| | |
|---|---|
| Compound 9 | 25% |
| "Perminal" BX | 1% |
| "Dispersol" T | 5% |
| Polyvinylpyrrolidone | 10% |
| Silica | 25% |
| China clay | 34% |

EXAMPLE 12

The ingredients set out below were formulated into a dispersible powder by mixing and grinding the ingredients in the proportions stated.

| | |
|---|---|
| Compound 2 | 25% |
| "Aerosol" OT/B | 2% |
| "Dispersol" A | 5% |
| China clay | 68% |

In Examples 4 to 12 the proportions of ingredients given are by weight.

The following constitutes an explanation of the compositions or substances represented by the various Trade Marks and Trade Names referred to in the foregoing Examples.

| | |
|---|---|
| "LUBROL" L | is a condensate of 1 mole of nonyl phenyl with 13 molar proportions of ethylene oxide. |
| "AROMASOL" H | is a solvent mixture of alkyl- |

-continued

| | |
|---|---|
| "DISPERSOL" T AND AC | benzenes. is a mixture of sodium sulphate and a condensate of formaldehyde with the sodium salt of naphthalene sulphonic acid. |
| "LUBROL" APN 5 | is a condensate of 1 mole of nonyl phenol with 5½ moles of naphthalene oxide. |
| "CELLOFAS" B 600 | is a sodium carboxymethyl cellulose thickener. |
| "LISSAPOL" NX | is a condensate of 1 mole of nonyl phenol with 8 moles of ethylene oxide. |
| "AEROSOL" OT/B | is dioctyl sodium sulphosuccinate. |
| "PERMINAL" BX | is an alkyl naphthalene sulphonate (sodium salt). |

EXAMPLE 13

The compounds were tested against a variety of foliar fungal diseases of plants. The technique employed was as follows.

The plants were grown in John Innes Potting Compost (No. 1, or Seed, as appropriate) in 4 cm diameter mini-pots. A layer of fine sand was placed at the bottom of the pot to facilitate uptake of test compound by the roots.

The test compounds were formulated either by bead-milling with aqueous Dispersol T or as a solution in acetone/ethanol which was diluted to the required concentration immediately before use. For the foliage diseases, 100 p.p.m. a.i. suspensions were sprayed on to the foliage and applied to the roots of the same plant via the soil. (Sprays were applied to maximum retention, and root drenches to a final concentration equivalent to approximately 40 ppm a.i./dry soil). Tween 20, to give a final concentration of 0.1%, was added when the sprays were applied to the cereals.

For most of the tests, the test compound was applied to the soil (roots) and/or to the foliage (by spraying) one or two days before the plant was inoculated with the diseases. An exception was the test on *Erysiphe graminis*, in which the plants were inoculated 24 hours before treatment. After inoculation, the plants were put into an appropriate environment to allow infection to take place and then incubated until the disease was ready for assessment. The period between inoculation and assessment varied from 4 to 14 days according to the disease and environment.

The disease control was recorded by the following grading in which the percentages represent the extent of the disease as a percentage of the disease on the unsprayed control plants.

4 = No disease
3 = 0–5%
2 = 6–25%
1 = 26–60%
0 = >60%

The results are shown in Table II.

TABLE II

| | DISEASE CONTROL | | | | | |
|---|---|---|---|---|---|---|
| Compound No | *Puccinia recondita* in wheat | *Phytophthora infestans* in tomato | *Plasmopara vitacola* in vines | *Piricularia oryzae* in rice | *Botrytis cinerea* in tomatoes | *Erysiphe graminis* in barley |
| 1 | 0 | 4 | — | 0 | 1 | 4 |
| 2 | 0 | 0 | 0 | 0 | 1 | 3 |
| 3 | 0 | 0 | 0 | 1 | 1 | 2 |
| 4 | 1 | 2 | 0 | 0 | 3 | 3 |
| 5 | 1 | — | 0 | 0 | 0 | 4 |
| 6 | 0 | 0 | 4 | 0 | 1 | 4 |
| 7 | 0 | 3 | — | 1 | 1 | 4 |
| 8 | 0 | 0 | — | 1 | 3 | 4 |
| 9 | 1 | — | 4 | 0 | 3 | 4 |
| 10 | 0 | 0 | 0 | 0 | 0 | 3 |
| 11 | 0 | 0 | 1 | 0 | 1 | 3 |
| 12 | 1 | 2 | 0 | 0 | 0 | 3 |
| 13 | 1 | 3 | 0 | — | 2 | 4 |
| 14 | 0 | 0 | 0 | 0 | 2 | 2 |
| 15 | 1 | 0 | 0 | 1 | 2 | 2 |
| 16 | 1 | 0 | 0 | 1 | 3 | 3 |
| 17 | 1 | 0 | 0 | 1 | 3 | 2 |
| 18 | 0 | 0 | 0 | — | 0 | 3 |
| 20 | 0 | 0 | 0 | 0 | 1 | 2 |
| 21 | 0 | 0 | 0 | 0 | 0 | 2 |
| 22 | 0 | 0 | 0 | 1 | 0 | 3 |
| 25 | 0 | 0 | 0 | — | 0 | 3 |
| 26 | 0 | 1 | 0 | 0 | 3 | 2 |
| 27 | 0 | 2 | 0 | 0 | 0 | 3 |
| 28 | — | 0 | 0 | 3 | 1 | 2 |
| 29 | 0 | 2 | 0 | 0 | 2 | 4 |
| 30 | — | 3 | 0 | 3 | 3 | 2 |
| 31 | 0 | 0 | 0 | 0 | 0 | 2 |
| 32 | 0 | 0 | 0 | 0 | 0 | 2 |
| 33 | 0 | 0 | 0 | 1 | 0 | 2 |
| 34 | 0 | 0 | 0 | 0 | 0 | 1 |
| 36 | 0 | 0 | 0 | 3 | 2 | 4 |
| 38 | 0 | 0 | 0 | — | 0 | 0 |
| 39 | 0 | 0 | 0 | — | 0 | 1 |
| 43 | 0 | 2 | 0 | 2 | 2 | 1 |
| 44 | 0 | 2 | 0 | 0 | 0 | 3 |
| 45 | 0 | 0 | 0 | 0 | 3 | 4 |
| 46 | 0 | 0 | 0 | 2 | 1 | 3 |
| 47 | 0 | 0 | 0 | 0 | 0 | 2 |
| 48 | 0 | 2 | 0 | 0 | 2 | 2 |

EXAMPLE 14

This Example illustrates the herbicidal properties of the compounds.

Each compound (0.12 g) was mixed with 5 ml of an emulsion prepared by diluting 100 ml of a solution containing 21.8 grams per liter of Span 80 and 78.2 grams per litre of Tween 20 in methylcyclohexanone to 500 ml with water. Span 80 is a Trade Mark for a surface-active agent comprising sorbitan monolaurate. Tween 20 is a Trade Mark for a surface-active agent comprising a condensate of sorbitan monolaurate with 20 molar proportions of ethylene oxide. The mixture of the compound and the emulsion was shaken with glass beads and then diluted to 12 ml with water.

The spray composition so prepared was sprayed onto young pot plants (post-emergence test) of the species named in Table III below, at a rate equivalent to 1000 liters per hectare. (10 Kilograms of the test compound per hectare).

Damage to plants was assessed 14 days after spraying by comparison with untreated plants, on a scale of 0 to 3 where 0 is 0 to 25% damage and 3 represents 75 to 100% kill. In a test for pre-emergence herbicidal activity, seeds of the test species were placed on the surface of fibre trays of soil and were sprayed with the compositions at the rate of 1000 liters per hectare. The seeds were then covered with further soil. Fourteen days after spraying, the seedlings in the sprayed fibre trays were compared with the seedlings in unsprayed control trays, the damage being assessed on the same scale of 0 to 3.

The results are given in Table III below.

TABLE III

| COMPOUND | TIME OF APPLICATION | Le | To | Ot | Dg | Ll | Cn |
|---|---|---|---|---|---|---|---|
| 1 | Pre | 2 | 2 | 3 | 3 | 3 | 3 |
|  | Post | 1 | 0 | 0 | 0 | 0 | 0 |
| 4 | Pre | 3 | 3 | 2 | 3 | 3 | 0 |
|  | Post | 2 | 0 | 0 | 3 | 0 | 0 |
| 5 | Pre | 0 | 0 | 0 | 0 | 0 | 0 |
|  | Post | 2 | 0 | 0 | 2 | 0 | 0 |
| 6 | Pre | 3 | 3 | 3 | 3 | 3 | 3 |
|  | Post | 2 | 0 | 0 | 3 | 0 | 0 |
| 7 | Pre | 2 | 3 | 3 | 3 | 3 | 0 |
|  | Post | 2 | 0 | 0 | 3 | 0 | 0 |
| 10 | Pre | 2 | 2 | 3 | 3 | 3 | 1 |
|  | Post | 2 | 3 | 0 | 2 | 0 | 0 |
| 3 | Pre | 1 | 0 | 0 | 1 | 1 | 0 |
|  | Post | 1 | 0 | 0 | 1 | 0 | 0 |
| 9 | Pre | 3 | 2 | 2 | 3 | 3 | — |
|  | Post | 3 | 3 | 1 | 3 | — | 0 |
| 11 | Pre | 3 | 2 | 0 | 3 | 3 | — |
|  | Post | 3 | 3 | 1 | 2 | — | 0 |
| 12 | Pre | 2 | 1 | 2 | 3 | 3 | — |
|  | Post | 2 | 1 | 0 | 3 | 0 | 0 |
| 13 | Pre | 3 | 2 | 3 | — | 3 | 0 |
|  | Post | 0 | 3 | 0 | 3 | 0 | — |
| 14 | Pre | 2 | 2 | 1 | — | 3 | 0 |
|  | Post | 1 | 2 | 0 | 1 | 0 | — |
| 16 | Pre | 2 | 2 | 0 | — | 3 | 0 |
|  | Post | 3 | 3 | 0 | 1 | 0 | 0 |
| 18 | Pre | 1 | 0 | 0 | — | 3 | 0 |
|  | Post | 2 | 1 | 0 | 1 | 0 | — |
| 19 | Pre | 2 | 2 | 0 | — | 3 | 0 |
|  | Post | 0 | 1 | 0 | 1 | 0 | 0 |
| 20 | Pre | 2 | 1 | 0 | — | 1 | 0 |
|  | Post | 0 | 0 | 0 | 3 | 0 | 0 |
| 21 | Pre | 2 | 0 | 0 | — | 3 | 0 |
|  | Post | 1 | 0 | 0 | 0 | 0 | 0 |
| 22 | Pre | 3 | 1 | 3 | — | 3 | 0 |
|  | Post | 3 | 3 | 0 | 1 | 0 | 0 |
| 23 | Pre | 2 | 0 | 0 | — | 3 | 0 |
|  | Post | 1 | 0 | 0 | — | 0 | 0 |

TABLE III-continued

| COMPOUND | TIME OF APPLICATION | Le | To | Ot | Dg | Ll | Cn |
|---|---|---|---|---|---|---|---|
| 24 | Pre | 3 | 3 | 3 | — | 3 | — |
|  | Post | 1 | 1 | 0 | — | 0 | 0 |
| 26 | Pre | — | 2 | 3 | — | 3 | 0 |
|  | Post | 2 | 0 | 0 | — | 0 | 0 |
| 27 | Pre | 2 | 2 | 2 | — | 3 | 0 |
|  | Post | 2 | 0 | 0 | — | 0 | 0 |
| 29 | Pre | 3 | 3 | 3 | — | 3 | 3 |
|  | Post | 3 | 3 | 1 | 3 | 0 | 0 |
| 32 | Pre | 3 | 0 | 0 | — | 3 | 0 |
|  | Post | 1 | 2 | 0 | 0 | 0 | 0 |
| 34 | Pre | 3 | 2 | 3 | — | 3 | 0 |
|  | Post | 2 | 3 | 3 | 3 | 3 | 3 |
| 35 | Pre | 3 | 3 | 3 | — | 3 | 3 |
|  | Post | 3 | 3 | 0 | 0 | 0 | 0 |
| 36 | Pre | 3 | 3 | 3 | — | 3 | 0 |
|  | Post | 3 | 3 | 0 | 0 | 0 | 0 |
| 37 | Pre | 2 | 0 | 0 | — | 3 | — |
|  | Post | 2 | 0 | 0 | 0 | 0 | 0 |
| 38 | Pre | 2 | 1 | 0 | — | 3 | 0 |
|  | Post | 1 | 3 | 0 | — | 0 | 0 |
| 39 | Pre | 2 | 2 | 3 | — | 3 | — |
|  | Post | 2 | 3 | 0 | — | 0 | 0 |
| 40 | Pre | 3 | 3 | 3 | — | 3 | — |
|  | Post | 2 | 3 | 0 | — | 0 | 0 |
| 41 | Pre | 3 | 3 | 3 | — | 3 | — |
|  | Post | 2 | 3 | 0 | — | 0 | 0 |
| 42 | Pre | 3 | 3 | 3 | — | 3 | 3 |
|  | Post | 0 | 2 | 0 | 0 | 0 | 1 |
| 44 | Pre | 1 | 2 | 0 | — | 3 | 0 |
|  | Post | 2 | 2 | 0 | — | 0 | 0 |
| 45 | Pre | 2 | 3 | 3 | — | 3 | 1 |
|  | Post | 3 | 0 | 0 | — | 0 | 0 |
| 46 | Pre | — | 3 | 3 | — | 3 | 3 |
|  | Post | 1 | 0 | 0 | — | 0 | 0 |
| 47 | Pre | 3 | 3 | 0 | 2 | 3 | 3 |
|  | Post | 3 | 2 | 0 | — | 0 | 0 |
| 49 | Pre | 3 | 3 | 3 | 3 | 3 | 0 |
|  | Post | 3 | 3 | 0 | 3 | 3 | 0 |
| 50 | Pre | 1 | 1 | 0 | 1 | 3 | 0 |
|  | Post | 2 | 0 | 0 | 3 | 0 | 0 |
| 51 | Pre | 3 | 3 | 3 | 3 | 3 | — |
|  | Post | 3 | 3 | 0 | 3 | 1 | 0 |

The names of the test species were as follows:
Le — Lettuce
To — Tomato
Ot — Oats. Cultivated oats are used in the pre-emergence test and wild oats (*Avena fatua*) are used in the postemergence test.
Dg — *Digitaria sanguinalis*
Ll — *Lolium perenne*
Cn — *Cyperus rotundus*

EXAMPLE 15

This Example further illustrates the herbicidal properties of various compounds of the invention. Tests were carried out as described in Example 15 but using a wider range of test species and various rates of application. The pre-emergence test was also carried out in a slightly different way. The seeds of the plants were sown in a shallow slit formed in the soil, sprayed and then covered with more soil. The results are given in Table IV, in terms of a number on the scale 0 to 5 where 0 is 0 to 20% damage and 5 is complete kill.

TABLE IV

|  | Rate Of Application | Time Of Application (HG 1 Hectare) | Sb | Rp | Ct | Sy | Mz | Ww | Rc | Sn | Ip | Am | Pi | Ca | Po | Xa | Ab | Cv | Ot | Dg | Pa | St | Ec | Sh | Ag | Cn |
|---|---|---|---|---|---|---|---|---|---|---|---|---|---|---|---|---|---|---|---|---|---|---|---|---|---|---|
|  | 1.0 | Pre | 0 | 0 | 0 | 0 | 0 | 0 | 0 | 0 | 0 | 0 | 0 | 2 | 3 | — | 0 | — | 0 | 5 | 4 | 5 | 4 | — | 0 | 0 |
| 1 | 1.0 | Post | 3 | 1 | 2 | 1 | 0 | 0 | — | 0 | 0 | 0 | 0 | 0 | 0 | — | 0 | 0 | 0 | -0 | 0 | 0 | 0 | 0 | 0 |
|  | 5.0 | Pre | — | — | 0 | 0 | 4 | 4 | 5 | 3 | — | 5 | 3 | 3 | 4 | 0 | 3 | — | 5 | 5 | 5 | 5 | 5 | — | 0 | 0 |
|  | 5.0 | Post | 0 | — | 0 | 0 | 0 | 0 | 0 | 0 | 0 | 1 | 0 | 0 | 3 | 0 | 0 | 0 | 0 | 1 | 0 | 0 | 0 | 0 | 0 |
|  | 5.0 | Pre | 2 | 0 | 0 | 0 | 0 | 3 | 0 | — | 2 | 4 | 0 | 4 | 4 | — | 1 | — | 2 | 4 | 4 | 4 | 3 | — | — | 0 |
| 4 | 5.0 | Post |  |  |  |  |  |  |  |  |  | INACTIVE |  |  |  |  |  |  |  |  |  |  |  |  |  |  |
|  | 1.0 | Pre | 4 | 0 | 0 | 0 | 0 | — | 0 | — | 1 | 0 | 0 | 0 | 0 | 0 | 3 | — | 0 | 0 | 0 | 0 | 0 | — | — | 0 |

TABLE IV-continued

| Rate Of Application | Time Of Application (HG 1 Hectare) | TEST PLANTS | | | | | | | | | | | | | | | | | | | | |
|---|---|---|---|---|---|---|---|---|---|---|---|---|---|---|---|---|---|---|---|---|---|---|
| | | Sb | Rp | Ct | Sy | Mz | Ww | Rc | Sn | Ip | Am | Pi | Ca | Po | Xa | Ab | Cv | Ot | Dg | Pa | St | Ec | Sh | Ag | Cn |
| 5.0 | Pre | 3 | 1 | 0 | 2 | 4 | 4 | 4 | — | 2 | 5 | 4 | 3 | 4 | — | 2 | — | 4 | 5 | 5 | 5 | 5 | — | — | 0 |
| 6 5.0 | Post | 3 | 1 | 3 | 3 | 4 | — | 0 | 0 | 3 | 4 | 1 | 3 | — | 3 | 3 | 2 | 0 | 4 | 1 | 2 | 0 | 0 | 0 | 0 |
| 1.0 | Pre | 3 | 0 | 0 | 0 | 3 | 4 | 0 | — | 0 | 5 | 1 | 0 | 4 | — | 2 | — | 0 | 4 | 4 | 4 | 4 | — | — | 0 |
| 5.0 | Pre | 0 | 0 | 0 | 0 | 0 | 4 | 0 | — | 0 | 0 | 3 | 4 | 4 | — | 0 | — | 4 | 5 | 5 | 4 | 0 | — | — | 0 |
| 7 5.0 | Post | 2 | 0 | 3 | 0 | 0 | — | 0 | 0 | 1 | 4 | 1 | 1 | — | 0 | 0 | 0 | 0 | 2 | 0 | 2 | 0 | 0 | 0 | 0 |
| 1.0 | Pre | INACTIVE | | | | | | | | | | | | | | | | | | | | | | | | |

The names of the test plants in Table IV are as follows:

Sb — Sugar beet
Rp — Rape
Ct — Cotton
Sy — Soyabean
Mz — Maize
Ww — Winter wheat
Rc — Rice
Sn — *Senecio vulgaris*
Ip — *Ipomoea purpurea*
Am — *Amaranthus retroflexus*
Pi — *Polygonum aviculare*
Ca — *Chenopodium album*
Po — *Portulaca oleracea*
Xa — *Xanthium pensulvanicum*
Ab — *Abutilon theophrasti*
Cv — *Convolvulus arvensis*
Ot — Oats
Dg — *Digitaria sanguinalis*
Pu — *Poa Annua*
St — *Setaria viridis*
Ec — *Echinochloa crus-galli*
Sh — *Sorghum halepense*
Ag — *Agropyron repens*
Cn — *Cyperus rotundus*

It will be seen from Table III that compounds 1, 4, 6 and 7 show pronounced selectivity in their herbicidal action, having good pre-emergence herbicidal activity against *Graminae* species, for example, *Digitaris sanguinalis*, *Setaria virides* and *Echinochloa crus-galli*, with good tolerance to broad-leaved crops at an application rate of 5 hg 1 hectare. The best selectivity is shown towards cotton and soyabean.

We claim:
1. A compound of the formula:

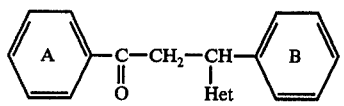

wherein rings A and B are unsubstituted, or carry one or more substituents, each substituent being a lower alkyl radical; a fluorine, chlorine, bromine, or iodine atom; a lower alkoxy radical; a cyano group; a nitro group; a lower alkylcarbonyloxy radical; a methylenedioxy radical; an amino group; or a mono- or di- lower alkyl substituted amino group, and wherein Het stands for a 1,2,4-triazol-1-yl radical, at least one of the rings A and B being substituted; and salts of compounds of the foregoing formula.

2. Compounds as claimed in claim 1 wherein ring A is unsubstituted and ring B is substituted.

3. Compounds as claimed in claim 2 wherein ring B carries a 2-chloro or 2-fluoro substituent.

4. Salts of compounds as claimed in claim 1, wherein the salts are formed from alkali metals, alkaline earth metals, ammonia, or primary, secondary, or tertiary aliphatic amines in which the 1, 2 or 3 aliphatic radical each contain from 1 to 6 carbon atoms.

5. A method of killing or severely damaging unwanted plants, which comprises applying to the locus of the plants, an effectively lethal or severely damaging amount of a compound of the formula:

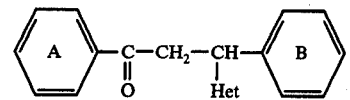

wherein rings A and B are unsubstituted, or carry one or more substituents, each substituent being a lower alkyl radical; a fluorine, chlorine, bromine, or iodine atom; a lower alkoxy radical; a cyano group; a nitro group; a lower alkylcarbonyloxy radical; a methylenedioxy radical; an amino group; or a mono- or di-lower alkyl substituted amino group, and wherein Het stands for a 1,2,4-trizol-1-yl radical; or a salt of the compound of the foregoing formula.

6. A method as claimed in claim 5 wherein the rate of application of the compound is from 0.25 to 10.0 kilograms per hectare.

7. A method of selectively inhibiting the growth of grass weeds in broadleaved crops, which comprises applying to the locus of the crop, in an amount sufficient to inhibit the growth of grass weeds but insufficient substantially to damage the crop, a compound of the formula:

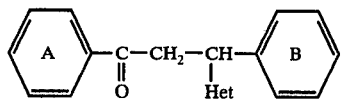

wherein rings A and B are unsubstituted, or carry one or more substituents, each substituent being a lower alkyl radical; a fluorine, chlorine, bromine, or iodine atom; a lower alkoxy radical; a cyano group; a nitro group; a lower alkylcarbonyloxy radical; a methylenedioxy radical; an amino group; or a mono- or di-lower alkyl substituted amino group, and wherein Het stands for a 1,2,4-triazol-1-yl radical; or a salt of the compound of the foregoing formula.

8. A pesticidal composition, comprising a pesticidally effective amount of a compound of the formula:

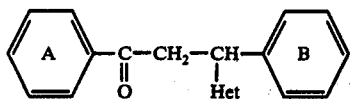

wherein rings A and B are unsubstituted, or carry one or more substituents, each substituent being a lower alkyl radical; a fluorine, chlorine, bromine, or iodine atom; a lower alkoxy radical; a cyano group; a nitro group; a lower alkylcarbonyloxy radical; a methylenedioxy radical; an amino group; or a mono- or di-lower alkyl substituted amino group, and wherein Het stands for a 1,2,4-triazol-1-yl radical at least one of the rings A and B being substituted; or a salt of the compound of the foregoing formula in admixture with an inert carrier comprising a solid diluent, or a liquid diluent containing a surface-active agent.

* * * * *